United States Patent [19]

King

[11] Patent Number: 5,041,421
[45] Date of Patent: Aug. 20, 1991

[54] FRAGRANT MATERIAL

[75] Inventor: Michael L. King, Decatur, Ill.

[73] Assignee: Mari-Mann Herb Co., Inc., Decatur, Ill.

[21] Appl. No.: 428,176

[22] Filed: Oct. 27, 1989

Related U.S. Application Data

[63] Continuation-in-part of Ser. No. 266,792, Nov. 3, 1988, abandoned.

[51] Int. Cl.$^5$ .............................................. A61K 7/46
[52] U.S. Cl. ........................................ 512/4; 424/76.3; 424/76.4; 424/84
[58] Field of Search ................. 512/1, 2, 5; 424/76.3, 424/76.4, 84; 426/4

[56] References Cited

U.S. PATENT DOCUMENTS

| | | |
|---|---|---|
| 3,371,984 | 3/1968 | Kelly et al. ........................ 424/76.4 |
| 3,446,893 | 5/1969 | Hanford et al. .......................... 2/4 |
| 3,449,266 | 6/1969 | Cashman et al. ...................... 512/4 |
| 3,943,243 | 3/1976 | Koak .................................. 424/76.3 |
| 4,071,616 | 1/1978 | Black ................................. 424/76.4 |
| 4,196,851 | 4/1980 | Davis ..................................... 512/4 |
| 4,226,829 | 10/1980 | Mike ..................................... 512/4 |
| 4,244,059 | 1/1981 | Pflaumer ............................... 512/4 |
| 4,285,905 | 8/1981 | Feit .................................. 424/76.4 |
| 4,346,840 | 8/1982 | Gaiser et al. ........................... 512/4 |
| 4,427,366 | 1/1984 | Moore ................................. 431/291 |
| 4,579,717 | 4/1986 | Gyulay ................................ 422/125 |
| 4,767,741 | 8/1988 | Kelley et al. ........................... 512/4 |

FOREIGN PATENT DOCUMENTS

| | | | |
|---|---|---|---|
| 2 603 806 | 3/1988 | France ................................. 512/4 |
| 2603806 | 3/1988 | France ................................. 512/4 |
| 58-112541 | 7/1983 | Japan ............................... 424/76.4 |
| 58-185161 | 10/1983 | Japan ............................... 424/76.1 |
| 60-99256 | 6/1985 | Japan ............................... 424/76.3 |
| 61-57236 | 3/1986 | Japan ................................. 512/4 |

OTHER PUBLICATIONS

Applicant's knowledge of rock salt fragrance products.
Applicant's knowledge of plastic, starch and wax fragrant products.
Sale of "Sit-R-Simmer" products.
Sale of foam plastic pearls.

*Primary Examiner*—James H. Reamer
*Attorney, Agent, or Firm*—Fish & Richardson

[57] ABSTRACT

A fragrant material that imparts a pleasant fragrance when set out at ambient temperature or when placed in heated water. The fragrant material comprises an aggregate of small sodium chloride granules such as are produced by vacuum granulation, the granules formed into a molded shape, e.g. as a plurality of discrete pellets, or in a loose state, and having a fragrant oil and optionally a water soluble dye dispersed in the material. Also disclosed is a fragrant material comprising the combination of salt granules with a minor amount of finely divided inert particles, and a water-soluble dye. Other features that enhance performance and enable the product to be of low cost are also described.

39 Claims, No Drawings

FRAGRANT MATERIAL

CROSS REFERENCE

This application is a continuation in part of U.S. application Ser. No. 07/266,792 filed Nov. 3, 1988, by Michael L. King and entitled "Fragrant Material", now abandoned.

FIELD OF THE INVENTION

This invention relates to fragrant material for imparting a pleasant fragrance to a room, and the like.

BACKGROUND OF THE INVENTION

Man has imparted pleasant fragrances to rooms since time immemorial. Flowers, eucalyptus leaves, dill, and incense have been used for this purpose for thousands of years and are still widely used today. A wide variety of fragrant oils are now commercially available, but they are rarely used by themselves for providing fragrance to rooms because of their rapid evaporation rate and because of the danger of spills. Instead, fragrant oils are generally incorporated into a solid carrier, also known as a fixative. A number of different prior art carriers are or have been used with fragrant oils. For example, Moore, U.S. Pat. No. 4,427,366, discloses wax chips containing a fragrant oil and Gyulay, U.S. Pat. No. 4,579,717, discloses a porous ceramic ring which absorbs a fragrant oil. Another well known carrier is a mixture of dried Orris root, dried Calamus root, and other dried plant material which, when scented with a fragrant oil, is commonly sold as potpourri Rock salt to which fragrance oils have been applied has also been sold. However, none of these carriers is ideal.

An ideal carrier for a fragrant oil, depending upon the application, would exhibit many specific properties. First, the carrier would readily absorb fragrant oils and would leave no surface film which might cause staining or tackiness. Second, the carrier would also readily absorb dyes to permit the carrier to be dyed a color corresponding to the fragrance if desired. Third, the carrier would be odorless so as to not clash with the fragrance of the oil. Fourth, it would be nonflammable, nontoxic, nonallergenic, non nutritive and environmentally safe for obvious safety reasons. Fifth, for particular applications, an ideal carrier would consist of discrete particles having an average size of about $\frac{1}{4}$ to 1 inch with little or no fines. Such particles can be easily mixed, poured, and handled; they attractively fill up bowls and containers of various sizes and shapes; and, if spilled, can be picked up by hand. Sixth, the carrier would not soften or melt at elevated temperatures of 100° to 130° F. which are encountered in closed houses and automobiles during summer months. Seventh, the carrier would be relatively inexpensive and readily available.

Furthermore, an ideal carrier would be suitable for "simmering"—warming the material in or out of water to accelerate the flow of fragrance into the room. More particularly, the carrier would dissolve slowly in water, cause no harm to pots and pans and permit an easy clean up after use.

A large number of potential carriers were considered and/or tested and then rejected before the fragrant material of this invention was discovered. For example, potpourri crumbles into fines and leaves a messy residue after simmering in hot water. Wood chips exhibit similar disadvantages and have too strong an odor. Sugar cubes readily absorb oils and dyes, but become sticky and attract bugs. Starch readily absorbs oils and dyes, but cannot be easily formed into lasting solid shapes, attracts bugs and leaves a messy residue when used with water. Rock salt does not absorb oil and dye well because of its structure. Wax chips must be melted to incorporate the fragrant oil and dye, release little fragrance until they are heated, and create a mess if placed directly into hot water. Porous ceramic materials have limited absorbency, are expensive, and present a danger if broken because of the sharp and jagged edges of the pieces. Cellulose fibers are dry and absorb oils and dyes, but are not water soluble and are expensive. Vermiculite is also dry and will absorb oils, but will not dye well, is not water soluble, and is expensive. Accordingly, until the fragrant material of this invention was discovered, there existed a strong demand for a better solid carrier for fragrant oils.

SUMMARY OF THE INVENTION

The object of this invention is to provide an improved fragrant material for imparting a pleasant fragrance to a room or the like. A more particular object is to provide such a fragrant material which can be set out at ambient temperature in a room or placed in heated water.

I have discovered a fragrant material which meets these objects. According to one aspect of the invention, the material comprises a plurality of discrete pellets of compressed salt having a fragrant oil dispersed within the pellets. This fragrant material exhibits many advantages over other types of fragrant material which have been previously used in homes. The material has no surface film so it is non-staining. The material is odorless, nonflammable, nontoxic, nonallergenic, non nutritive, environmentally safe, homogeneous, non-crumbling with a high pressure break strength, and does not melt even at elevated temperatures. The material is relatively inexpensive and can be easily mixed with other fragrant materials. Furthermore, this material dissolves slowly in water, does not harm pots and pans, and can be easily cleaned after use. Finally, because the fragrant oil, and dye if present, is uniformly dispersed throughout the pellets, a partial dissolution of the pellets does not remove all the fragrant oil and dye from the pellets.

In another aspect, the invention features a fragrant material for imparting a pleasant fragrance when exposed in dry state at ambient conditions or when placed in heated water, that includes a molded shape of compressed sodium chloride salt granules having a fragrant oil dispersed within the molded shape.

Preferred embodiments of this aspect of the invention include additional features. A plurality of the molded shapes in the form of pellets are provided having an average size of approximately $\frac{1}{4}$ to 1 inch. The granules of the molded shape comprise vacuum granulated sodium chloride. The fragrant material additionally includes a dye dispersed within the molded shape. The fragrant material is formed by the process of applying the fragrant oil to the surface of a pre formed shape of the compressed salt granules and allowing the oil to be absorbed into the pores between the granules; preferably the oil is applied by spraying. The fragrant material is formed by the process of applying the fragrant oil to a loose aggregation of granules of sodium chloride and thereafter compressing the granules into the molded shape; preferably high molding pressure is employed to form the molded shape.

In another aspect, the invention features a fragrant material for imparting a pleasant fragrance when exposed in dry state at ambient conditions or when placed in heated water, that includes an aggregation of small vacuum granulated sodium chloride granules and a fragrant oil dispersed within the aggregation. In addition to including embodiments in which the aggregation of granules has been formed into a molded shape, this aspect of the invention also includes embodiments in which the small salt granules remain loose as a powder.

In embodiments of the various aspects of the invention described above, certain additional features are preferred. Most of the sodium chloride granules are about 850 microns or less in size. The aggregation includes a minor amount of finely divided, inert, water insoluble, hygroscopic particles that increase the carrying capacity of the mixture for the fragrant oil; preferably these particles are selected from the group consisting of silicon dioxide, calcium silicate, magnesium carbonate, tricalcium phosphate and sodium silicoaluminate and mixtures and combinations thereof; preferably they have a particle size of about 10 microns; preferably the weight ratio of the finely divided particles to the fragrant oil is about 1 to 3; preferably the finely divided particles comprise about 2% or more by weight of the fragrant material and more preferably to enhance a fragrancing effect as described while still being economical, the finely divided inert particles comprise more than about 3% but less than about 10% by weight of the fragrant material. The fragrant oil of the fragrant material includes an organic carrier fluid selected from diethylphthalate, methyl dihydroabietate, Hercolyn D, propylene glycol, dipropylene glycol, isoparaffins, Losol, saltrol, polysorbate, D limonene, glycerine and Isopar M; preferably the fragrant oil has a viscosity under ambient conditions of about 10 centipoise or more, preferably on the order of between about 10 and 20 centipoise. The fragrant material further includes a dye which is soluble in water, and perferably also in oil; the dye preferably is a polymer-bound azo colorant.

In another aspect, the invention features a dry, loose mixture comprising at least an aggregation of a large number of small vacuum granulated sodium chloride granules, a relatively minor amount of finely divided, inert, water insoluble, hygroscopic particles and a fragrant oil dispersed within the aggregation.

Another aspect of the invention is a fragrant material for imparting a pleasant fragrance when exposed in dry state at ambient conditions or when placed in heated water the fragrant material comprising an aggregation of small anhydrous salt granules and a minor amount of finely divided, inert, water soluble, hygroscopic particles, the finely divided inert particles selected from the group consisting of silicon dioxide, calcium silicate, magnesium carbonate, tricalcium phosphate and sodium silicoaluminate and mixtures and combinations thereof, the aggregation carrying a fragrant oil, the weight ratio of the finely divided particles to the fragrant oil being about 1 to 3, the salt granules in the fragrant material being selected so that in the presence of the inert particle they are dimensionally stable under ambient conditions.

Preferred embodiments also include selection of the ingredients to preform various functions The fragrant oil is selected to perform as a room freshener. The fragrant oil is selected to mask a pervading odor such as, for example, an animal odor. The fragrant material is adhered as a coating to an object to which it is desired to impart a fragrance. A dry mixture may be, for example, formulated to mask a pervading odor, e.g., in the form of a rug freshener.

The invention also includes the methods of forming the various materials described above.

DETAILED DESCRIPTION OF THE INVENTION

In certain important embodiments of the invention the fragrant material of this invention comprises discrete pellets of compressed salt, fragrant oil, and, optionally, dye. If the fragrant material is going to be simmered in water, it is preferred that the salt contain minimum amounts of insolubles. If the fragrant material is not going to be simmered, the purity of the salt is not critical. The preferred type of salt is sodium chloride (NaCl) because of its low cost and ready availability. The physical form of the pellet is compressed granular salt. This form has a high pressure break strength and yet is still extremely absorbent because of the microscopic pores between the compressed salt granules. For certain applications, the salt pellets have an average size of approximately ¼ to 1 inch, or about the size of marbles. For many applications, pellets of a smaller size tend to dissolve too quickly in water and are difficult to pick up if spilled, while pellets of a larger size dissolve too slowly in water and are not as attractive when placed in small bowls and containers. The shape of the pellet is not critical and spheres, cubes, cylinders, and the like are acceptable. There is no requirement that the shape and size of the pellets be uniform and, in fact, some variation is aesthetically pleasing. One preferred form of salt pellet is of the type used commercially to recharge water softeners. A representative example of such a pellet is the Morton ® System Saver ™ water softening pellet. These pellets typically contain about 99.70 percent sodium chloride and are about 1 inch long, ⅝ inch wide, and ⅜ inch thick.

A fragrant oil is a concentrated liquid fragrance. The fragrant oil may be derived from natural sources or may be synthetic. The oil generally contains a variety of organic compounds of differing volatilities. The particular type of fragrant oil is not critical to this invention and many suitable fragrant oils are commercially available. A more complete discussion of fragrant oils is found at Volume 14, page 717, et seq. under the heading "Perfumes" in the Kirk-Othmer Encyclopedia of Chemical Technology (2d Ed. 1967).

The optional dye is a substance which imparts color to the fragrant material. The dye may be available as a powder or as a liquid. Dyes which are water soluble are generally preferred because they have less tendency to stain and can be cleaned more easily. The particular dye used in this invention is a matter of choice and many suitable dyes having good color stability and retention are commercially available.

The relative amounts of salt pellets and fragrant oil in the material is a matter of choice which depends upon the strength of the fragrance in the oil and the desired strength of the fragrance in the fragrant material. The weight ratio of salt pellets to fragrant oil is generally about 20:1 to 100:1, and preferably about 30:1 to 50:1. If excessive amounts of fragrant oil are used, the saturation point of the salt pellets may be exceeded and the pellets may have an undesirable "wet" surface. If a dye is used, its quantity is also a matter of choice.

It is found while achieving a dry-to-the-touch character it is possible to include larger amounts of fragrant oil in the material by addition of the finely divided inert additive mentioned above in quantities greater than what might ordinarily be included as free flowing agents in common salt. (In the prior art such agents have been used for the purpose of making salt free flowing or capable of being compressed into the form of a pellet.) The quantity of the particles is generally about 2% or more; in many cases, especially for free flowing powder embodiments, in the range of about 3 to 10% of the total weight of the fragrant material is employed.

Further details concerning preferred ingredients and uses will be given following the description of certain examples.

EXAMPLE 1

An 80 pound plastic film bag of Morton ® Salt Pellets was opened and the contents gently poured into an enamel cast-iron 60 gallon tub. The salt pellets are a commercial product of the Morton Salt Division of Morton Thiokol, Inc., Chicago, Ill. They are compressed from vacuum granulated salt and contain a minimum of 99.5 percent sodium chloride. The dimensions of a typical pellet are 1 inch long, ⅝ inch wide, and 3.8 inch thick.

Two pounds of peach fragrant oil, a commercial product of The Lebermuth Company, South Bend, Ind., are poured into a standard 2.5 gallon hand sprayer. Two ounces of Liquidtint Yello BL dye, a commercial product of the Millikin Dye Company, Inman, S.C., are then poured into the sprayer. The sprayer is then sealed and vigorously shaken to uniformly mix the fragrant oil and dye.

The sprayer is then pumped to generate pressure and the contents are sprayed upon the pellets. The pellets are mixed during spraying to obtain uniform distribution. After spraying, the pellets are allowed to sit for about one hour to allow complete absorption of the oil and dye. The fragrant material is then screened to remove fines and packaged.

EXAMPLE 2

This example is formed by application of a fragrant oil to salt granules prior to compression of the granules to form a pellet. A vanilla-creme fragrance containing vanilla-creme fragrant oil, Ethyl Vanillin, and Coumarin is obtained. (The fragrance supplier may include small quantities of other ingredients according to its recipe). The fragrance components are added to approximately 30% carrier fluid (Diethyl Phthalate) forming a fragrant oil with the following properties:

| | |
|---|---|
| Specific Gravity @20° C. (water = 1) | 1.1328–1.1338 |
| Refractive Index @25° C. | 1.5155–1.5165 |
| Vapor Density (AIR = 1) | >1 |
| Boiling Point (of most volatile component >1%) | over 175° C. |
| Solubility in water | neglible |
| Appearance and odor | colorless to pale yellow liquid with a strong vanilla fragrance. |

The fragrant oil is then added to an anhydrous dendretic sodium chloride salt including about 2 percent of Cabosil. About 2.5% of fragrant oil by weight is added to the salt (about 50 lbs. oil per 2000 lbs. of salt). The fragrant oil is mixed with the salt and Cabosil mixture to form a slurry. The slurry is gravity fed into a tablet press that exerts close to 1500 lb./sq. in. of pressure, achieving temperatures close to 806° C. (near the melting point of NaCl granules at the high pressure), which results in fusion of the granules, with the formation of "bridging" areas where the granules are bonded together. After tabletizing the final pellets are extremely hard, shiny, solid and have a glazed appearance and are stable, non-crumbling, and smell like vanilla.

In use, with respect to the foregoing examples, there is no need of inducing an airflow because the fragrance is sufficiently strong to disperse on its own. The pellet or tablets will "fragrance" an average sized open room of 100 sq. ft. for at least 6 months, and are also highly water soluble.

A by product of producing the pellets or tablets is the extra powder or granules that are vibrated off through a screen. This powder has all the properties of the pellets or tablets except that it is in powder form. It is found to have a number of practical applications, for instance, for placing in heated water, or as a fragrance powder, e.g. to mask a pervading odor such as the smell of urine.

EXAMPLE 3

A fragrant material is formed by application of a fragrant oil to salt granules prior to compression of the granules to form a pellet A cinnamon fragrance containing cinnamon fragrant oil, Cinnamine Aldehyde, Cinnamon Leaf Oil and Ethyl Vanillin is obtained. The fragrance components are added to approximately 20% carrier fluid (7% Hercolyn-D, 13% dipropylene glycol), forming a fragrant oil with the following properties:

| | |
|---|---|
| Specific Gravity @20° C. (water = 1) | 1.048–1.058 |
| Refractive Index @25° C. | 1.581–1.591 |
| Vapor Density (AIR = 1) | 1 |
| Boiling Point (of most volatile component 1%) | over 175° C. |
| Solubility in water | Neglible |
| Appearance and odor | pale yellow liquid with a cinnamon fragrance. |

The fragrant oil is mixed with dye. By volume, 3 cc yellow Chromatech dye and 9 cc red Chromatech dye per 1 lb. of oil are used. The dyed fragrant oil is added to dendritic sodium chloride salt and about 2 percent Cabosil. About 2.5% of fragrant oil by weight is added to the salt (50 lb. oil/2000 lb. of salt). The oil is mixed with the salt to form a slurry and processed as in Example 2.

EXAMPLE 4

In this example, a loose form (powder) fragrant material is formed by application of a fragrant oil to a mixture of salt granules and particles that enhance carrying capacity. The material is formed as powder by addition of a fragrant oil to a non-compressed mixture of salt granules and a small amount of the finely divided particles. The amount of the enhancing particles is used in excess of 3% and generally less than about 10% by weight of the amount of salt, in this example, 5%.

A wintergreen fragrance containing wintergreen fragrant oil, peppermint, spearmint and wintergreen oil is obtained. The fragrance components are added to approximately 40% carrier fluid (isoparaffins), forming a fragrant oil with the following properties:

| | |
|---|---|
| Specific Gravity @20° C. (water = 1) | .885 |
| Refractive Index @25° C. | 1.464 |
| Vapor Density (AIR = 1) | >1 |
| Boiling Point (of most volatile component 1%) | 155° C. |
| Solubility in water | Neglible |
| Appearance and odor | colorless to slightly yellow liquid with a minty wintergreen scent. |

The fragrant oil is mixed with dye. By volume, 1 cc yellow Chromotech dye and 0.1 cc blue Chrometech dye per 1 lb. of oil are used. The dyed fragrant oil is added to TFC 999 salt (salt treated at manufacture with yellow prussiate of soda anticaking agent) and about 5% calcium silicate. About 9.5% of fragrant oil by weight is added to the salt (95 lb. oil to 1000 lb. of salt). The oil is slowly added and mixed thoroughly with the salt and particles to form a loose dry mixture. The resulting product is a dry to the touch, free flowing and made up of hard, shiny small granules.

Due to the electrostatic properties of the salt the resulting powder may be easily applied in a spraying fashion to many different surfaces electrostatically. It also may be added to water for fragrancing a room by simmering.

Ingredients

Preferably, anhydrous vacuum granulated sodium chloride salt crystals are employed such as Morton Thiokol Food Grade 999 salt which has a granule size distribution of 98% less than 850 microns, and 51% less than 425 microns, (Morton Thiokol, Chicago, Ill.) or a vacuum granulated dendritic sodium chloride salt, e.g. Morton Thiokol Star Flake ® or Dendritic ES ® salt (latter includes 0.5% sodium silicoaluminate) which have a granule size distribution of 98% less than 425 microns and 65% less than 210 microns. Dendritic salts have a modified, high surface area, porous, crystalline structure which may enhance absorption of fragrant oil and therefore increase the life of the fragrant product or the amount of scent provided to the atmosphere or both. It will be understood that the granules may be much smaller, e.g. the size of a fine powder. In some cases, other anhydrous metal halide salts such as calcium or potassium chloride may be employed.

Examples of inert particles for enhancing the fragrant oil carrying capacity are particles which are inert, water insoluble, hygroscopic, ultrafine (generally less than 10 microns in size) particles such as silicon dioxide (e.g. Cabosil, Cabot Corporation available in some salts purchased from Morton Thiokol), calcium silicate, magnesium carbonate, tricalcium phosphate and sodium silicoaluminate (e.g. Zeolex available from J. H. Huber, Havre DeGrace, Md.) or a combination thereof. Preferably, the particles are used when the amount of fragrant oil required in the material is above the saturation point, i.e., the point where the amount of fragrant oil causes the material to become wet to the touch. For sodium chloride granules of the size here involved, the saturation point is about 2% by weight of fragrant oil. The finely divided particles are added at about one part (by weight) agent to every 3 parts fragrant oil. In pellet materials, the amount of fine particle agent is typically about 2% or more by weight. For example, to incorporate about 6.5% by weight of fragrant oil, the material may include about 2% by weight of the enhancing particles. In fragrant materials of loose granular form, the amount of the finely divided inert particles is typically greater than about 3% by weight, but in the interest of limiting cost, less than about 10%. It will be understood that combinations of various types of particles can be formulated to take advantage of specific properties of the specific particles. For example, loose form fragrant materials may use a combination of silicon dioxide and magnesium carbonate. Silicon dioxide has greater fragrant oil holding effectiveness, while magnesium carbonate is less dusty. It will also be understood that an amount of particles greater than the 1 to 3 ratio may be used to enhance the free flowing character of a loose mixture material or make pelletizing easier when applying fragrant oil to granules prior to pelletizing.

As previously indicated, it is well known that a fragrant oil is a concentrated liquid fragrance containing a variety of organic compounds of differing volatilities and viscocities. It is composed of natural and/or essential oils, and/or aroma chemicals (a liquid or crystalline fragrant chemical) and normally includes a carrier fluid such as propylene glycol. The carrier fluids generally are non-fragrancing, non-volatile, miscible with the fragrant ingredients and non reactive. Such fragrant oils are moderately viscous. A cinnamon fragrant oil as described in Example 3 has a viscocity of 10 cps at 25° C. and vanilla fragrant oil as described in Example 2, has a viscocity of 20 cps at 25° C. (as measured on a Brookfield Viscometer model LVT at 30 Rpm). A particular carrier fluid may be selected to enhance the physical properties such as dryness, hardness, and shiny appearance of the resultant fragrant material. It may also be selected to change the evaporative rate of the fragrant oil thus to change the perceived strength in the sense of smell and the length of time of fragrancing. Examples of suitable carriers include diethylphthalate, Hercolyn (methyl dihydroabietate), Hercolyn hydrogenated methyl ester of Rosin (available as Hercolyn D from the Lebermuth Co., Inc), propylene glycol, dipropylene glycol, isoparaffins, saltrol, Losol ($C_9$-$C_{11}$ isoparaffins) (available from Shaw Mudge and Co.), Isopar M (isoparaffin) (available from R. N. Eaton and Co., Inc) polysorbate, D limonene, and glycerin. The carrier fluid can also be selected to serve as an anti hardening agent in powder form products. A combination of various carrier fluids can also be used.

Generally, an essential oil and additional carrier fluid are formulated prior to application to the granules to have a moderately high viscosity, i.e., preferably in the range of about 10 to 20 cps. If the viscosity is too low the fragrant oil will not remain on the salt and the material will be wet to the-touch. If too high, fragrancing will be insufficient.

For embodiments which apply fragrant oil prior to pelletizing, choice of press pressure can also affect the fragrancing strength. Increasing the press pressures, e.g. from 1500 lb/sq. in. to the range of 1600 lb/sq. in. to 1800 lb/sq. in. allows the amount of fragrant oil to be decreased without sacrificing fragrant strength.

The dye, preferably water as well as oil miscible, may be added directly to the fragrant oil for application to the salt granules. The dye is typically a polymer bound azo colorant (e.g. Liquitints made by Milliken Chemical, Division of Milliken and Co. available from Chromatech, Inc.).

For producing a practical fragrant material with a new fragrance, one may follow the following procedures to achieve a strongly fragrancing product that lasts for a protracted duration and is dry-to the-touch.

As a first step, a fragrance is obtained from a fragrance supplier. The combinations of chemical components for a particular fragrance that give rise to certain characteristic smells, also known as "notes", are selected, on a subjective trial basis to provide a pleasing odor, in general, as strong as possible. The fragrance may be selected by simply smelling a sample of the liquid. It will be understood that the fragrant oil with a desireable scent may in some cases be simply purchased from a vendor and used directly as described herein, or sometimes it may be modified. For example, for a vanilla fragrance, a certain amount of coumarin may also be added to make it smell somewhat like cotton candy.

After selection of the fragrance, the fragrant oil is evaluated for use on salt granules. It is practical to begin with a fragrant oil that incorporates the carrier fluid ordinarily used by the fragrance vendor for such type of a fragrance.

The evaluation can use water softener pellets formed of salt granules (as in Example 1) regardless of whether the fragrant oil will be applied to a preformed pellet (as in Example 1), salt granules compressed into pellets after application of the fragrant oil (as in Examples 2 and 3) or salt granules that are to remain loose as a powder material (as in Example 4).

For the evaluation, a bag full of water softener pellets is thoroughly mixed with a two to five percent by weight fragrant oil by pouring the oil in the bag, shaking the bag so the oil is coated around the pellets and taking 10 to 15 of the pellets out of the bag and setting them out in the air. Preferably to speed up the test, the pellets are put under a conventional desk fan. The pellets are then subjected to practical observations to determine if there is excessive powdering and to determine if there is excessive wetness. If there is no powdering or wetness, the viscosity of the oil can be considered to be above the minimum required. If the surface is powdered or if the oil wicks out from the material and the surface is wet, the viscosity is too thin, indicating that a more viscous carrier fluid should be added. In general, to obtain a suitable product, different trials may be performed with carrier fluids having different viscosities depending on the degree of degradation observed.

Generally, the evaluation for physical properties can be made after the elapse of four hours. Degradation is easiest to observe around rough edges of the pellet. If the material shows no visible signs of degradation within four hours under a fan, the fragrant oil carrier fluid will generally produce materials that have satisfactory physical properties, but if a higher degree of assurance is desired, a longer time may be employed for the observation.

For determining the fragrancing ability of the fragrant oil and carrier, the pellets are placed in a 10 ft.×10 ft. room for about a day and a panel of experienced testers, selected for their acuity of smell, are asked for their impressions. If the room is judged by them to have a pleasant degree of fragrance by the end of the day, the fragrancing properties will be satisfactory.

If there are negative observations of physical properties or fragrancing capabilities, change in the carrier fluid of the fragrant oil is made to provide more fragrancing or better physical properties.

In general, a higher viscosity carrier fluid is used if it is desired to enhance the physical properties, decrease fragrancing power, and extend fragrancing duration, while a lower viscosity carrier is used to enhance the strength of smell by achieving a higher evaporative rate.

The amount of change of viscosity that is appropriate depends on the type of fragrance and the carrier provided by the fragrance vendor. Four general catagories of fragrance are often recognized: fruit, floral, spice and citrus. Citrus and spice oils usually are thinner than floral and fruit oils and generally require addition of a more viscous carrier. The more viscous carriers include, for example, polysorbate (which is available in a variety of viscosities, a preferred grade used herein being Tween-20) or Hercolyn D. Less viscous carriers include, for example, dipropylene glycol or diethylphtlalate.

Carrier fluids that are known by the industry to work well (provide pleasant fragrancing in the liquid state) with a particular fragrance may not perform well on salt granules. For instance, with cinnamon fragrance, dipropylene glycol is often used in the industry. Observations as described have indicated this carrier fluid is too thin in the particular circumstances of example 3. Addition of 7% Hercylon D, (as described in Example 3) produces a more viscous carrier that achieves better results.

Additional Uses

Pellets or loose granules may be glued together or onto other products; examples include: decorative wreaths, baskets, wooden crafts, and other craft type items. The pellets may be glued together in combination to form shapes, such as a ball, teddybear, tree, house, etc. Promotions like the scratch and sniff products are also possible. The pellets also can be pressed into desired shapes. A unique fragrance may be created by choosing a combination of differently treated pellets or granules and joining them together.

Uses for loose granules or powder include incorporation into potpourri, powdered chemical substances, roach powder or a rug cleaner, powdered pet deodorizers, and fragrancing scents. In addition, the powder may be used to coat surfaces (e.g. by electrostatic methods). Plastic garbage bags are one possible application. The powder may also be incorporated within the plastic. Other uses include locker room balls or "Locker Balls TM" for YMCA's, health clubs, schools, and athletic teams (preferably with a strong citrus odor, e.g. lemon orange) to mask the smell of sweat, mold, and body odor. Other uses include steam room or sauna tablets, or "Spa Balls TM", for example, with menthol and/or eucalyptus oil. The Spa Balls TM would slowly melt, be about the size of golf balls (e.g. 400 grains) and would last three to five days. Other sizes and shapes for varied time uses could also be used, for example, a small 100 grain ball that lasts just 1 day. Other uses include therapeutic uses, for example, aroma therapy, using a known stimulant type fragrant oil, such as lemon oil. The materials can also be employed as an insecticide or insect repellent by selection of certain herbal oils capable of insecticide or repellent activity. For example, cedar oil can be used to repel moths, also pennyroyal, mint, wormwood, and lavender repel fleas and ticks, tansy repels ants. Southernwood oil can also be used as well as other insect repellant and insecticide botanical oils.

What is claimed is:

1. A fragrant material for imparting a pleasant fragrance, the fragrant material comprised predominantly of compressed small sodium chloride granules in a dimensionally stable molded shape having a fragrant oil dispersed within the molded shape, said material being substantially water soluble, environmentally safe, dimensionally stable under ambient conditions and having a lasting fragrancing effect.

2. The fragrant material of claim 1 comprising a plurality of said molded shapes in the form of pellets having an average size of approximately ¼ to 1 inch.

3. The fragrant material of claim 1 wherein the granules of the molded shape comprises vacuum granulated sodium chloride.

4. The fragrant material of claim 1 additionally comprising a dye dispersed within the molded shape.

5. The fragrant material of claims 1, 2, 3 or 4 produced by the process of applying the fragrant oil to the surface of a pre-formed shape of compressed salt granules and allowing the oil to be absorbed into the pores between the granules.

6. The fragrant material of claim 5 wherein the process of production includes providing a plurality of said preformed shapes in the form of pellets and applying the fragrant oil thereto by spraying.

7. The fragrant material of claim 1, 2, 3 or 4 formed by the process of applying the fragrant oil to a loose aggregation of granules of sodium chloride and thereafter forming the granules into said molded shape.

8. The fragrant material of claim 7 formed by the process of compressing the granules under high pressure to form the molded shape.

9. A fragrant material for imparting a pleasant fragrance, the fragrant material comprised predominantly of an aggregation of small vacuum granulated sodium chloride granules and a fragrant oil dispersed within said aggregation, said material being environmentally safe, dimensionally stable under ambient conditions and having a lasting fragrancing effect.

10. The fragrant material of claim 1 or 9 wherein most of said sodium chloride granules are about 850 microns or less in size.

11. The fragrant material of claim 1 or 9 including a minor amount of finely divided, inert, water insoluble, hygroscopic particles.

12. The fragrant material of claim 11 wherein said finely divided inert particles are selected from the group consisting of silicon dioxide, calcium silicate, magnesium carbonate, tricalcium phosphate and sodium silicoaluminate and mixtures and combinations thereof.

13. The fragrant material of claim 10 wherein said finely divided inert particles have a particle size of about 10 microns.

14. The fragrant material of claim 11 wherein the weight ratio of said finely divided particles to said fragrant oil is about 1 to 3.

15. The fragrant material of claim 11 herein said finely divided inert particles comprise about 2% or more by weight of said fragrant material.

16. The fragrant material of claim 11 wherein said finely divided inert particles comprise more than about 3% and less than about 10% by weight of said fragrant material.

17. The fragrant material of claim 1 or 9 wherein said fragrant oil includes an organic carrier fluid selected from diethylphthalate, methyl dihydroabietate, Hercolyn D, propylene glycol, dipropylene glycol, isoparaffins, Losol, saltrol, polysorbate, D limonene, glycerin and Isopar M and mixtures and combinations thereof.

18. The fragrant material of claim 17 wherein the fragrant oil has a viscosity under ambient conditions on the order of about 10 cps or more.

19. The fragrant material of claim 18 wherein said viscosity is on the order of about 10 to 20 centipoise.

20. The fragrant material of claim 1 or 9 further including a dye which is soluble in water.

21. The fragrant material of claim 20 wherein said dye is soluble in oil.

22. The fragrant material of claim 21 wherein said dye is a polymer-bound azo colorant.

23. The fragrant material of claim 1 or 9 wherein said fragrant oil is selected to perform as a room freshener.

24. The fragrant material of claim 1 or 9 wherein said fragrant oil is selected to mask a pervading odor.

25. The fragrant material of claim 24 wherein said odor is an animal odor.

26. The fragrant material of claim 1 or 9 adhered as a coating to an object to which it is desired to impart a fragrance.

27. The fragrant material of claim 1 or 9 wherein said fragrance acts on an insect repellant.

28. The fragrant material of claim 1 or 9 wherein said material is suitable for therapeutic use.

29. The fragrant material of claim 1 or 9 wherein said material is a locker room ball.

30. The fragrant material of claim 1 or 9 wherein said material is a steam room or suana ball.

31. A dry, loose mixture comprised predominantly of at least a large number of small vacuum granulated sodium chloride granules, a relatively minor amount of finely divided, inert, water insoluble, hygroscopic particles and a fragrant oil dispersed in the mixture of said granules and particles, said material being substantially water soluble, environmentally safe, dimensionally stable under ambient conditions and having a lasting fragrancing effect.

32. The dry, loose mixture of claim 31 in the form of rug freshner.

33. A fragrant material for imparting a pleasant fragrance, the fragrant material comprised predominantly of compressed sodium chloride salt granules in a molded shape in the form of a pellet about 1 inch long, ⅜ inch wide and ⅜ inch thick having a fragrant oil dispersed within the molded shape and produced by the process of applying the fragrant oil to the surface of a pre-formed pellet and allowing the oil to be absorbed into the pores between the granules, said material being substantially water soluble, environmentally safe and stable under ambient conditions.

34. The fragrant material of any one of claims 1, 9 or 31, 33 wherein sodium chloride makes up about 90% or more by weight of said product.

35. The fragrant material of any one of claims 1, 9, 31, or 33 wherein said material is exposed in a dry state to fragrance a room at ambient conditions.

36. The fragrant material of any one of claims 1, 9, 31, or 33 wherein said fragrant material is mixed with a dry powdered active substance.

37. The fragrant material of claim 1, 9, 31, or 33 wherein said fragrant material is placed in heated water.

38. The fragrant material of claim 5 or 33 wherein said preformed shape is a water softener pellet of the type used to recharge water softeners.

39. The fragrant material of claim 5 wherein said shape is a pellet about 1 inch long, ⅜ inch wide and ⅜ inch thick.

* * * * *

UNITED STATES PATENT AND TRADEMARK OFFICE
CERTIFICATE OF CORRECTION

PATENT NO. : 5,041,421

DATED : August 20, 1991

INVENTOR(S) : Michael L. King

It is certified that error appears in the above-identified patent and that said Letters Patent is hereby corrected as shown below:

On title page, item [56]
Under Foreign Patent Documents

Delete "2603806 3/1988 France".

Under Other Publications add:

--Sale of Pepper Oil Salt Canning Tablets Formed of Salt Granules--;

Col. 1, line 32, insert --.-- after "potpourri".

Col. 3, line 52, insert --,-- after "water";
        line 66, insert --.-- after "functions".

Col. 6, line 27, insert --.-- after "pellet".

Col. 11, line 5, delete "under ambient conditions";
         line 6, after "effect" insert --under ambient conditions--.

Col. 11, line 37, delete "under ambient conditions";
         line 38, after "effect" insert --under ambient conditions--.

Col. 12, line 36, delete "under ambient conditions";
         line 37, after "effect" insert --under ambient conditions--.

UNITED STATES PATENT AND TRADEMARK OFFICE
CERTIFICATE OF CORRECTION

PATENT NO.   : 5,041,421

DATED        : August 20, 1991

INVENTOR(S)  : Michael L. King

It is certified that error appears in the above-identified patent and that said Letters Patent is hereby corrected as shown below:

Col. 12, line 49, after "safe" delete "and" and insert --,--.

Col. 12, line 50, after "stable" insert --and having a lasting fragrancing effect--.

Signed and Sealed this

Seventh Day of December, 1993

Attest:

*Attesting Officer*

BRUCE LEHMAN

*Commissioner of Patents and Trademarks*